(12) United States Patent
Karama et al.

(10) Patent No.: US 9,125,866 B1
(45) Date of Patent: Sep. 8, 2015

(54) ANTIDEPRESSANT COMPOUNDS

(71) Applicant: KING SAUD UNIVERSITY, Riyadh (SA)

(72) Inventors: Usama Sayed Karama, Riyadh (SA); Mujeeb Abdullah Saeed Sultan, Riyadh (SA); Kamal Eldin Hussein El Tahir, Riyadh (SA); Abdulrahman Ibrahim Almansour, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/608,042

(22) Filed: Jan. 28, 2015

(51) Int. Cl.
| | |
|---|---|
| *A61K 31/137* | (2006.01) |
| *C07C 211/42* | (2006.01) |
| *C07C 209/26* | (2006.01) |
| *A61K 31/135* | (2006.01) |
| *C07C 47/457* | (2006.01) |

(52) U.S. Cl.
CPC ............ *A61K 31/135* (2013.01); *C07C 47/457* (2013.01); *C07C 211/42* (2013.01); *C07C 2103/88* (2013.01)

(58) Field of Classification Search
CPC .......................... C07C 211/42; C07C 2103/88
See application file for complete search history.

(56) References Cited

U.S. PATENT DOCUMENTS

| 2,673,874 | A | | 3/1954 | Jenkins |
| 3,422,104 | A | * | 1/1969 | Schroter et al. ............... 544/154 |
| 3,455,928 | A | | 7/1969 | Schmidt et al. |
| 4,139,711 | A | | 2/1979 | Narisada |
| 5,192,762 | A | | 3/1993 | Gray et al. |
| 6,511,976 | B1 | | 1/2003 | Andres-Gil et al. |
| 8,524,766 | B2 | | 9/2013 | Sonesson et al. |

FOREIGN PATENT DOCUMENTS

| FR | 1332530 | 6/1963 |
| FR | 2769629 | 4/1999 |

OTHER PUBLICATIONS

I. Weiner et al., "A comparison of drug effects in latent inhibition and the forced swim test differentiates between the typical antipsychotic haloperidol, the atypical antipsychotics clozapine and olanzapine, and the antidepressants imipramine and paroxetine", Behavioural Pharmacology, (2003), vol. 14, pp. 215-222.
D.A. Slattery et al., "Using the rat forced swim test to assess antidepressant-like activity in rodents", Nature Protocols (2012), vol. 7, pp. 1009-1014 (Abstract only).
"CAS No. 7673-68-9 (9,10-dihydro-9,10-ethanoanthracene-11-carbaldehyde",printed from www.guidechem.com/cas-767/7673-68-9.html on Jul. 14, 2014, 2 pages.

* cited by examiner

*Primary Examiner* — Paul A Zucker
(74) *Attorney, Agent, or Firm* — Richard C Litman

(57) ABSTRACT

The antidepressant compounds are compounds of the formula:

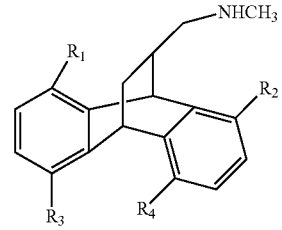

wherein $R_1$ and $R_2$ are either both hydrogen or both halogen (particularly chlorine), and if $R_1$ and $R_2$ are both hydrogen, $R_3$ and $R_4$ are both halogen (particularly chlorine), otherwise both $R_3$ and $R_4$ are hydrogen; or a pharmaceutically acceptable salt thereof. The compounds may be prepared by: (a) reducing 1,8-dihaloanthrquinone with zinc powder in aqueous ammonia, followed by acidic treatment to provide 1,8-dihaloanthracene; (b) Diels-Alder [4+2] cycloaddition reaction of the 1,8-dihaloanthracene and acrolein at room temperature in the presence of boron trifluoride etherate to obtain a mixture of the intermediate compounds 1,8-dihalo-9,10-dihydo-9,10-ethanoanthracene-11-carbaldehyde and 4,5-dihalo-9,10-dihydo-9,10-ethanoanthracene-11-carbaldehyde; (c) separating the mixture of carbaldehydes by column chromatography; and (d) direct reductive amination of the respective carbaldehydes to obtain the corresponding antidepressant compounds of the above formula.

16 Claims, 1 Drawing Sheet

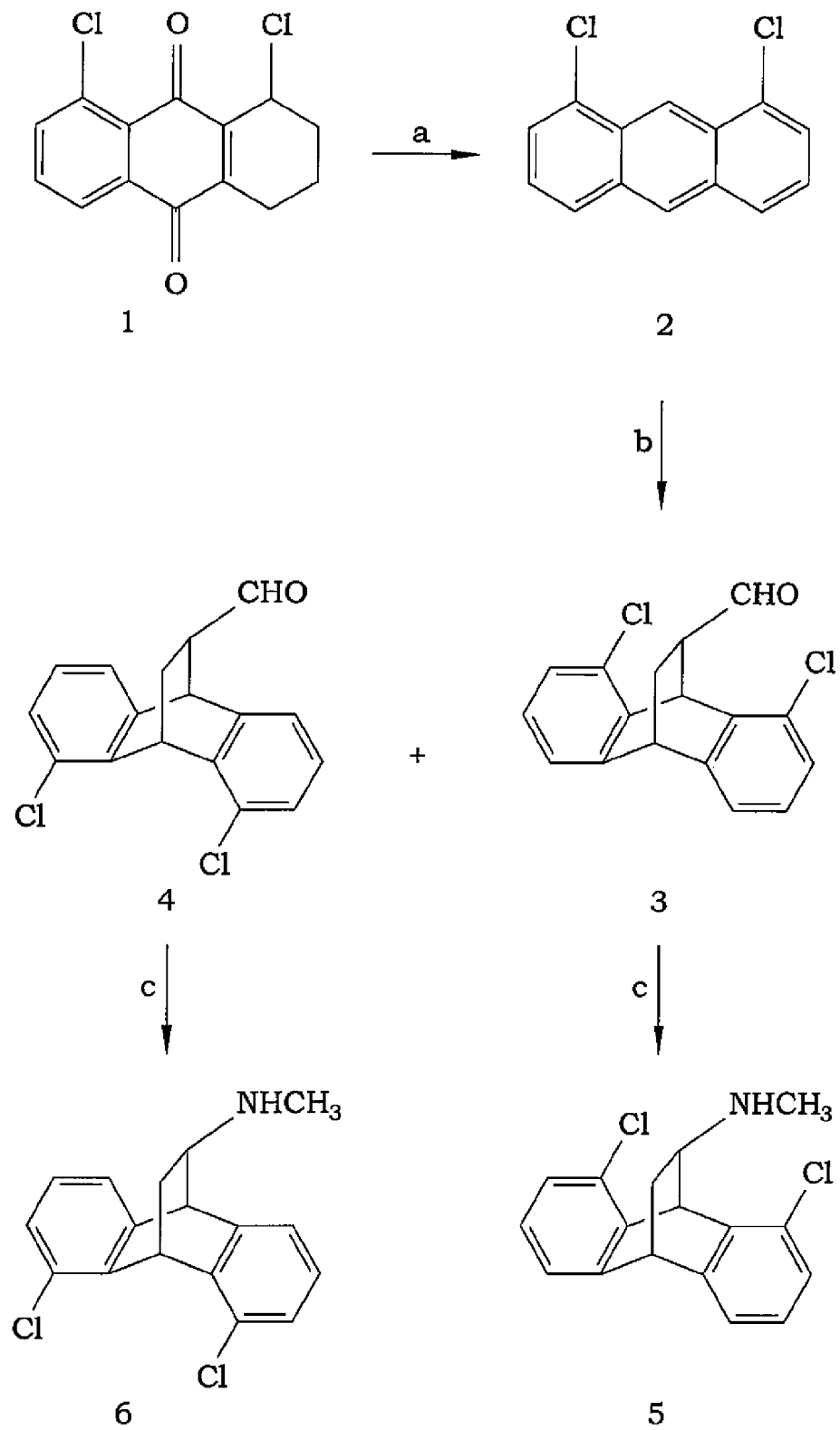

ANTIDEPRESSANT COMPOUNDS

BACKGROUND OF THE INVENTION

1. Field of the Invention

The present invention relates to antidepressants, and particularly to antidepressant compounds that are dichlorinated compounds of the dihydroethanoanthracene family.

2. Description of the Related Art

Depression is a mood disorder that causes a persistent feeling of sadness. The pharmacotherapy of depression started in the 1950s. There are currently ten to twenty different drugs marketed as antidepressants, depending on the country. Known antidepressants include selective serotonin reuptake inhibitors (SSRIs), atypical antidepressants, tricyclic antidepressants (TCAs), and monoamine oxidase inhibitors (MAOIs). Unfortunately, side effects are common in all antidepressants. Side effects of antidepressants are the main reason that many people stop a course of depression medication. Antidepressant and anxiolytic drugs without side effects are still being sought.

All of the selective serotonin reuptake inhibitor (SSRI) antidepressants, such as citalopram, escitalopram, fluoxetine, fluvoxamine, paroxetine and sertraline (brand names Zoloft® [Zoloft is a registered trademark of Pfizer Inc. of New York, N.Y.]) possess halogen atoms at specific positions, which are key determinants for the drugs' specificity for serotonin transporter (SERT). It is believed that halogen atoms can also increase lipophilicity, binding affinity, and membrane permeability to fill hydrophobic cavities in the protein binding site, to facilitate the blood-brain barrier crossing, and to prolong the lifetime of the drug, thereby improving bioavailability. However, the effects of introducing halogen atoms to a particular compound have been poorly studied. As such, many anxiolytic and antidepressant compounds do not include halogen atoms.

The tetracyclic drugs benzoctamine(9,10-dihydro-N-methyl-9,10-ethanoanthracene-9-methanamine) and maprotiline (9,10-dihydro-N-methyl-9,10-ethanoanthracene-9-propanamine) are bridged anthracene compounds that do not possess halogen atoms. Despite their structural similarity, benzoctamine is primarily an anxiolytic drug that exhibits antagonistic effects on norepinephrine, while maprotiline is an antidepressant and anxiolytic drug that is useful as a norepinephrine reuptake inhibitor. Seizures, leukopenia and skin reactions are common side effects of maprotiline.

Thus, antidepressants compounds solving the aforementioned problems are desired.

SUMMARY OF THE INVENTION

The antidepressant compounds are compounds of the formula:

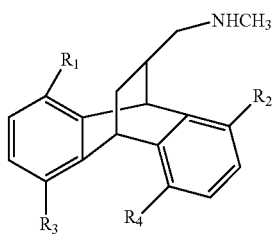

wherein $R_1$ and $R_2$ are either both hydrogen or both halogen (particularly chlorine), and if $R_1$ and $R_2$ are both hydrogen, $R_3$ and $R_4$ are both halogen (particularly chlorine), otherwise both $R_3$ and $R_4$ are hydrogen; or a pharmaceutically acceptable salt thereof.

The compounds may be prepared by: (a) reducing 1,8-dihaloanthrquinone with zinc powder in aqueous ammonia, followed by acidic treatment to provide 1,8-dihaloanthracene; (b) Diels-Alder [4+2] cycloaddition reaction of the 1,8-dihaloanthracene and acrolein at room temperature in the presence of boron trifluoride etherate to obtain a mixture of the intermediate compounds 1,8-dihalo-9,10-dihydo-9,10-ethanoanthracene-11-carbaldehyde and 4,5-dihalo-9,10-dihydo-9,10-ethanoanthracene-11-carbaldehyde; (c) separating the mixture of carbaldehydes by column chromatography; and (d) direct reductive amination of the respective carbaldehydes to obtain the corresponding antidepressant compounds of the above formula.

The antidepressant compounds also extend to the intermediate compounds having the formula:

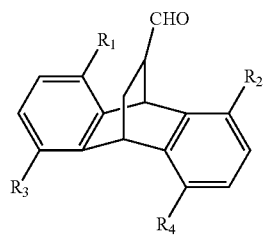

wherein $R_1$ and $R_2$ are either both hydrogen or both halogen (particularly chlorine), and if $R_1$ and $R_2$ are both hydrogen, $R_3$ and $R_4$ are both halogen (particularly chlorine), otherwise both $R_3$ and $R_4$ are hydrogen. The aldehyde functional group at C11 is relatively reactive, and the carbonyl group is sterically open, permitting synthesis of many derivatives of the dihalo-ethanoanthracene parent compound without impairing the antidepressive properties of the parent compound.

These and other features of the present invention will become readily apparent upon further review of the following specification and drawings.

BRIEF DESCRIPTION OF THE DRAWINGS

The sole diagram is an exemplary reaction scheme for synthesis of the antidepressant compounds according to the present invention.

DETAILED DESCRIPTION OF THE PREFERRED EMBODIMENTS

The antidepressant compounds are compounds of the formula:

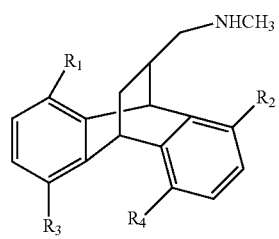

wherein $R_1$ and $R_2$ are either both hydrogen or both halogen (particularly chlorine), and if $R_1$ and $R_2$ are both hydrogen, $R_3$ and $R_4$ are both halogen (particularly chlorine), otherwise both $R_3$ and $R_4$ are hydrogen; or a pharmaceutically acceptable salt thereof.

The antidepressant compounds can include dihalo-9,10-dihydro-N-methyl-ethanoanthracene-11-methanamine (also named dihalo-11-methylaminomethyl-9,10-dihydro-9,10-ethanoanthracene) compounds or a pharmaceutically acceptable salt thereof. The antidepressant compounds can be used as an active ingredient of pharmaceuticals for the treatment of depression. The method of making the antidepressant compounds is exemplified herein by an example in which the halogen atoms are chlorine. However, it is believed that the same method may be employed for other halogens (bromine, fluorine, iodine), and that the final compounds have the same therapeutic effect as the dichloro examples described below.

The sole drawing FIGURE depicts a reaction scheme by which exemplary antidepressant compounds can be prepared. Referring to the drawing FIGURE, acrolein and 1,8-dichloroanthracene 2 can be reacted at room temperature in the presence of a catalytic amount of boron trifluoride etherate, through a Diels-Alder [4+2] cycloaddition reaction, to produce two isomeric cycloadducts 3 and 4. The compound 1,8-dichloroanthracene 2 can be obtained by the reduction of the commercially available 1,8-dichloroanthraquinone 1 with zinc powder in aqueous ammonia followed by an acidic treatment, in accordance with the procedure provided in the literature. The two isomeric cycloadducts 3 and 4 can be separated by column chromatography and converted to the desired amines 5 and 6 by direct reductive amination of the corresponding aldehyde. In the drawing FIGURE, the identifiers a, b, and c represent the solvents, reaction conditions, and yield, wherein a represents Zn, $NH_3/H_2O$, 100° C., 3 h, followed by HCl, isopropanol, 100° C., 3 h, 62%; b represents acrolein, $CH_2Cl_2$, $BF_3.OEt_2$, r.t., 3 h, 76%; and c represents $H_2$, Pd/C, $NH_2CH_3$, $CH_3OH$, r.t., 4 h, 85%.

The antidepressant compounds can be used to treat depression. As described in detail in the Examples below, the antidepressant compounds exhibited potential antidepressant activity when tested on mice subjected to the forced swim test. As exemplified in such technical articles as I Weiner et al., "A comparison of drug effects in latent inhibition and the forced swim test differentiates between the typical antipsychotic haloperidol, the atypical antipsychotics clozapine and olanzapine, and the antidepressants imipramine and paroxetine", Behavioural Pharmacology (2003), Vol. 14, pp. 215-22, and D. A. Slattery et al., "Using the rat forced swim test to assess antidepressant-like activity in rodents", Nature Protocols (2012), Vol. 7, pp. 1009-1014, the forced swim test is recognized in the pharmacological art as a standard test protocol for assessing antidepressant-like behavior induced by antidepressant compounds. The forced swimming test measures the duration of immobility of rodents exposed to the threat of drowning. Mice normally swim for 1-2 minutes and then turn helpless and become immobile. An immobile mouse is considered one that does not display any attempt to swim. For example, the mouse may appear to float, i.e. almost immobile and with its head above water. The majority of known antidepressant drugs decrease the duration of immobility. When the present antidepressant compounds were administered to the mice subjected to the forced swim test, a significantly shortened period of immobility was observed.

A pharmaceutically acceptable salt includes any non-toxic salt of the present antidepressant compounds, which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methyinitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate. A procedure for preparing pharmaceutically acceptable salts that may be used with the present antidepressant compounds is described in U.S. Pat. No. 3,422,104, issued Jan. 14, 1969, at col. 7, lines 44-62 and Example 3 (c). The '104 patent is hereby incorporated by reference in its entirety.

The antidepressant compounds can be administered to a patient in need thereof. For example, the antidepressant compounds can be used to treat a patient suffering from depression or depressive disorders. The depression or depressive disorders can include Major Depression with or without psychotic features, dysthymic disorder, bipolar disorders (I and II) and cyclothymic disorders.

The antidepressant compounds can be administered by any conventional route of administration, including, but not limited to, intravenous, oral, subcutaneous, intramuscular, intradermal and parenteral. Depending on the route of administration, the antidepressant compounds can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

Also provided is a pharmaceutical composition including an antidepressant compound. To prepare the pharmaceutical composition, one or more antidepressant compounds or salt thereof, as the active ingredient, is intimately admixed with a pharmaceutical carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. The tablets or pills can be coated or otherwise compounded to provide a dosage form affording the advantage of prolonged action. For example, the tablet or pills can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate. Examples of procedures for formulating the present antidepressant compounds as tablets and dragées cores are described in U.S. Pat. No. 3,422,104 at col. 19, line 63 through col. 22, line 75.

The antidepressant compound can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The antidepressant compound may also be coupled with soluble polymers as targetable drug carriers. Such polymers can include polyvinyl-pyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the antidepressant compound may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Preferably these compositions are in unit dosage forms such as tablets, pills, capsules, powders, granules, sterile parenteral solutions or suspensions, metered aerosol or liquid sprays, drops, ampoules, auto-injector devices or suppositories, for oral parenteral, intranasal, sublingual or rectal administration, or for administration by inhalation or insufflation. The composition can be presented in a form suitable for daily, weekly or monthly administration. The pharmaceutical compositions herein will contain, per dosage unit, e.g., tablet, capsule, powder, injection, teaspoonful, suppository and the like, an amount of the active ingredient necessary to deliver an effective dose as described above.

A therapeutically effective amount of the antidepressant compound or an amount effective to treat depression may be determined initially from in vivo assays described herein and adjusted for specific desired antidepressant compounds using routine methods. The therapeutically effective amount of the antidepressant compound can be about 20 mg/kg to about 80 mg/kg.

The following examples illustrate the present teachings.

Example 1

1,8-dichloroanthracene (2)

A suspension of 1,8-dichloroanthraquinone 1 (10.0 g, 36.1 mmol) and Zinc dust (50.0 g, 765 mmol) in 200 ml of aqueous 28% $NH_3$ was stirred for 3 h at 100° C. After cooling to room temperature, the resulting solid was separated by suction filtration. A $CH_2Cl_2$ solution of the resulting crude solid was combined with the $CH_2Cl_2$ extract of the supernatant liquid, and the mixture was dried over $MgSO_4$ and concentrated under vacuo. The residual crude solid was dissolved in a mixture of 500 ml of isopropanol and 50 ml of 12 M HCl. After the resulting solution had been refluxed for 3 h, it was concentrated and partitioned between $CH_2Cl_2$ and 5% $NaHCO_3$. The organic layer was collected and dried over $MgSO_4$. The solvent was evaporated, and the crude solid product was recrystallized from a $CH_2Cl_2$-hexane mixture. The collected product was allowed to dry in the air for 24 h to provide 5.5 g (62%) of 1,8-dichloroanthracene 2 as yellow needles: mp 153° C. IR (KBr): ν=1617, 1547, 1438, 1300, 1210, 953, 872, 775, 720, 678; $^1$H NMR (CDCl$_3$, 400 MHz) δ=7.25-7.88 (m; 6H, ArH), 8.36 (s; 1H, ArH-10), 9.16 (s; 1H, ArH-9); $^{13}$C NMR (CDCl$_3$, 400 MHz) δ=120.99, 125.68, 126.04, 127.33, 127.61, 132.63; MS (EI) m/z (%)=246 (100) [M$^+$], 248 (65); HRMS (EI) Calcd. For $C_{14}H_8Cl_2$ [M$^+$] 246.0003, Found 246.0001.

Example 2

Synthesis of 4,5-dichloro-9,10-dihydro-9,10-ethanoanthracene-11-carbaldehyde (3) and 1,8-dichloro-9,10-dihydro-9,10-ethanoanthracene-11-carbaldehyde (4)

Acrolein (1.65 ml, 23.8 mmol) was added to a solution of 1,8-dichloroanthracene 2 (1.23 g, 5 mmol) in 70 ml $CH_2Cl_2$, followed by dropwise addition of $BF_3 \cdot OEt_2$ (1.25 ml, 10.125 mmol). The mixture was stirred at room temperature for 3 h. During this time, the solution gradually turned brown, then the reaction was quenched with brine and extracted 3 times with $CH_2Cl_2$. The organic layer was collected and dried over $Na_2SO_4$, and the solvent was removed in vacuo. Column chromatography of the residue on silica gel (ethyl acetate/petroleum ether (1:10)) yields the aldehyde 3 ($R_f$=0.30) as Colorless oil (0.15 g, 10%) and the aldehyde 4 ($R_f$=0.41) as Colorless oil (1.0 g, 66%)

For compound (3), IR (KBr): ν=2924, 1725, 1576, 1435, 1260, 1167, 1046, 770, 704; $^1$H NMR (CDCl$_3$, 400 MHz): δ=2.01-2.04 (m; 1H, H-12), 2.10-2.12 (m; 1H, H-12), 2.81 (m; 1-H, H-11), 4.42 (t; J=2.64, 1H, H-9), 5.71 (d; J=2.52, 1H, H-10), 7.10-7.36 (m; 6H, ArH), 9.43 (d; J=1.76, 1H, CHO); $^{13}$C NMR (CDCl$_3$, 400 MHz): δ=27.89, 37.84, 44.34, 50.60, 122.20, 126.77, 127.65, 127.92, 129.78, 136.29, 138.48, 145.75, 146.18, 200.75; MS (EI) m/z (%)=302 (20) [M$^+$], 248 (85), 246 (100), 211 (5), 178 (4); HRMS (EI) Calcd. For $C_{17}H_{12}OCl_2$[M$^+$] 302.0265, Found 302.0266.

For compound (4), IR (KBr): ν=2944, 1727, 1577, 1455, 1210, 1167, 785, 770; $^1$H NMR (CDCl$_3$, 400 MHz): δ=2.04-2.07 (m; 1H, H-12), 2.11-2.12 (m; 1-H, H-12), 2.79 (m; 1H, H-11), 4.75 (d; J=2.52, 1H, H-10), 5.48 (t; J=2.76, 1H, H-9), 7.04-7.28 (m; 6H, ArH), 9.46 (d; j=1.44, 1H, CHO); $^{13}$C NMR (CDCl$_3$, 400 MHz): δ=26.96, 36.69, 45.53, 50.54, 122.10, 123.29, 127.11, 127.31, 129.78, 130.01, 141.50, 144.14, 201.72; MS (EI) m/z (%)=302 (20) [M$^+$], 248 (75), 246 (100), 212 (8), 178 (78); HRMS (EI) Calcd. For $C_{17}H_{12}Cl_2$ [M$^+$] 302.0265, Found 302.0265.

Example 3

Synthesis of 4,5-dichloro-9,10-dihydro-N-methyl-ethanoanthracene-11-methaneamine (5) and 1,8-dichloro-9,10-dihydro-N-methyl-ethanoanthracene-11-methaneamine (6)

In a two-necked round-bottomed flask 40 mg of 10% Pd/C was wetted with methanol and the flask was evacuated, then flushed with hydrogen two times. A solution of 100 mg (0.33 mmol) of aldehyde (3) (for synthesis of compound (5)) or aldehyde (4) (for synthesis of compound (6)) in 5 ml methanol was then added to the reaction mixture, followed by the addition of 0.5 ml, 2 M solution of methylamine in methanol. The mixture was stirred for 4 hours at room temperature under $H_2$ atmosphere (balloon). The reaction mixture was filtered through a pad of celite, and the solvent was removed in vacuo to yield 90 mg (85%) of the corresponding amine as white powder.

Compound (5) mp 290° C.; IR (KBr): ν=3440, 2942, 2864, 2775, 1592, 1457, 1410, 1026, 936, 755, 742, 555; $^1$H NMR (CDCl$_3$, 400 MHz) δ=1.27-1.37 (m; 1H, H-12), 2.13-2.19 (m; 1H, H-12), 2.47-2.50 (m; 1H—H-11), 2.55-2.66 (m; 5H—CH$_2$—N—CH$_3$), 4.31 (t; J=2.52, 1H, H-9), 4.63 (d; J=2.04, 1H, H-10), 6.98-7.05 (m; 3H, ArH), 7.17-7.19 (m; 2H, ArH), 7.45-7.48 (m; 1H, ArH); $^{13}$C NMR (CDCl$_3$, 500 MHz) δ=33.20, 33.93, 35.91, 43.71, 46.03, 54.70, 123.38, 123.52, 123.80, 125.62, 125.93, 126.08, 126.44, 139.33, 142.71, 142.98, 143.53

Compound (6) mp 310° C.; IR (KBr): ν=3435, 2943, 2774, 1626, 1593, 1457, 1411, 1027, 937, 758, 742, 555; $^1$H NMR (CDCl$_3$, 500 MHz) δ=1.24-1.26 (m; 1H, H-12), 2.04-2.08 (m; 1H, H-12), 2.38-2.40 (m; 1H, H-11), 2.45-2.54 (m; 5H—CH$_2$—N—CH$_3$), 4.21 (broad s; 1H, H-10), 4.52 (broad s; 1H, H-9), 6.98-7.05 (m; 3H, ArH), 7.17-7.19 (m; 2H, ArH), 7.42-7.43 (m; 1H, ArH); $^{13}$C NMR (CDCl$_3$, 500 MHz) δ=33.18, 33.60, 35.50, 43.59, 45.87, 54.36, 123.46, 123.57, 123.88, 125.69, 126.0, 126.17, 126.55, 139.11, 142.48, 142.85, 143.46; MS (EI) m/z (%)=318 (100) [M$^+$], 284 (22), 186(15), 117 (53); HRMS (EI) Calcd. for Cl8H18NCl$_2$ [M$^+$] 318.0816, Found 318.0809.

Example 4

Assessment of Antidepressant Activity Using the Forced Swim Test

To test for the presence of anti-depressant activity of the test compounds 3, 4, 5 and 6, the forced swim test was conducted on mice. The forced swimming test was conducted generally in accordance with the procedures set forth in David, D. J. P. et al., Psychopharmacology (2003), 166, 373-382, with the exception of a slight modification in the dimensions of the vessel used as a swimming pool. The vessel was a glass cylinder having an internal diameter of 25 cm and included water having a depth of 15 cm and a temperature of about 22±2° C. Swiss white mice weighing 25 g each were divided into 17 groups (N=4). One group served as control and the others divided for each test compound.

The test compounds were dissolved in DMSO and administered in 4 dose levels of 10, 20, 40, 80 mg/kg, respectively, intraperitoneally ("i.p."). The antidepressant compounds were administered to the mice 20 minutes before starting the swimming test. The control group was administered the vehicle only, in the same volume. Each mouse was allowed to stay in the swimming pool for 6 minutes. The duration of the period of immobility was measured at the beginning of the third minute of placing the mouse into the swimming pool and ended by the end of the sixth minute. In other words, the duration of immobility observed only during the last four minutes was recorded. For each test compound dose, the time of immobility was calculated and then averaged. Table 1 shows the effect of compounds 3, 4, 5 and 6 on mice subjected to the forced swimming test. Table 2 shows the percentage decrease in immobility times induced by each dose.

TABLE 1

Effects on Immobility Duration

| | Duration of immobility in seconds during the last four minutes of the six minute period | | | | |
|---|---|---|---|---|---|
| Animal Group | 0 mg/kg | 10 mg/kg | 20 mg/kg | 40 mg/kg | 80 mg/kg |
| Control | 225 ± 7 | | | | |
| Treated with 3 | | 240 | 240 | 160 ± 11* | 65 ± 4* |
| Treated with 4 | | 240 | 240 | 240 | 240 |
| Treated with 5 | | 240 | 200 ± 12.3 | 140 ± 7.9* | 36 ± 4.9* |
| Treated with 6 | | 240 | 240 | 240 | 30 ± 5* |

*P < 0.05, N = 4 compared with control

TABLE 2

Percentage decrease in Immobility Times

| Compound | Percentage decrease for dosage of 40 mg/kg | Percentage decrease for dosage of 80 mg/kg |
|---|---|---|
| 3 | 28.9 | 71.1 |
| 5 | 37.8 | 84.0 |
| 6 | — | 86.7 |

As shown in Tables 1 and 2, for mice treated with compounds 3, 5, or 6, a significant decrease in immobility time (p<0.05, N=4) was displayed compared with the control, at the 80 mg/kg dosage. Compounds 5 and 6 at the same dose were significantly more active than compound 3 (p<0.05, N=4). Only compounds 3, and 5 were significantly active in reducing immobility time at doses of 40 mg/Kg compared with control (p<0.05, N=4). Compound 4 was completely inactive in this test at all doses tested.

It is to be understood that the present invention is not limited to the embodiments described above, but encompasses any and all embodiments within the scope of the following claims.

We claim:

1. An antidepressant compound having the formula:

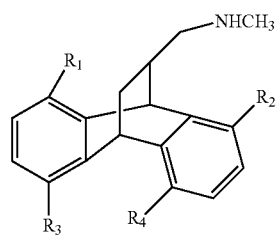

wherein R$_1$ and R$_2$ are either both hydrogen or both halogen, and if R$_1$ and R$_2$ are both hydrogen, R$_3$ and R$_4$ are both halogen, otherwise both R$_3$ and R$_4$ are hydrogen; or a pharmaceutically acceptable salt thereof.

2. The antidepressant compound according to claim 1, wherein R$_1$ and R$_2$ are both hydrogen, and R$_3$ and R$_4$ are both halogen.

3. The antidepressant compound according to claim 1, wherein R$_1$ and R$_2$ are both hydrogen, and R$_3$ and R$_4$ are both chlorine.

4. The antidepressant compound according to claim 1, wherein R$_3$ and R$_4$ are both hydrogen, and R$_1$ and R$_2$ are both halogen.

5. The antidepressant compound according to claim 1, wherein R$_3$ and R$_4$ are both hydrogen, and R$_1$ and R$_2$ are both chlorine.

6. A pharmaceutical composition, comprising an antidepressant compound according to claim 1 and a pharmaceutically acceptable carrier.

7. The pharmaceutical composition according to claim 6, wherein the antidepressant compound has the formula:

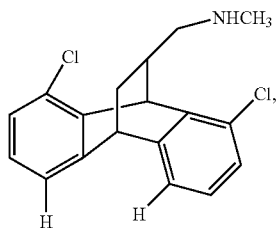 [SMILES: CNCC1CC2c3cccc(Cl)c3C1c1c(Cl)cccc12]

or a pharmaceutically acceptable salt thereof.

8. The pharmaceutical composition according to claim 6, wherein the antidepressant compound has the formula:

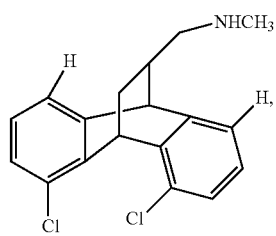

or a pharmaceutically acceptable salt thereof.

9. A method for treating depression, comprising the step of administering to a patient a therapeutically effective amount of the pharmaceutical composition according to claim 6.

10. A method of making an antidepressant compound of claim 1, comprising the steps of:
   (a) reducing 1,8-dihaloanthraquinone with zinc powder in aqueous ammonia, followed by acidic treatment to provide 1,8-dihaloanthracene;
   (b) performing a Diels-Alder [4+2] cycloaddition reaction of the 1,8-dihaloanthracene and acrolein at room temperature in the presence of boron trifluoride etherate to obtain a mixture of the intermediate compounds 1,8-dihalo-9,10-dihydro-9,10-ethanoanthracene-11-carbaldehyde and 4,5-dihalo-9,10-dihydro-9,10-ethanoanthracene 11-carbaldehyde;
   (c) separating the mixture of carbaldehydes by column chromatography; and
   (d) aminating the respective carbaldehydes by direct reductive amination to obtain the corresponding antidepressant compounds of the formula:

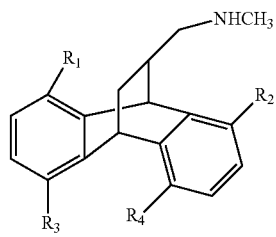

wherein $R_1$ and $R_2$ are either both hydrogen or both halogen, and if $R_1$ and $R_2$ are both hydrogen, $R_3$ and $R_4$ are both halogen, otherwise both $R_3$ and $R_4$ are hydrogen.

11. The method of making an antidepressant compound according to claim 10, wherein said step of reducing 1,8-dihaloanthraquinone with zinc powder in aqueous ammonia leaves a crude solid product, said acidic treatment comprising refluxing the crude solid product in a mixture of isopropanol and 12 M HCl for about three hours, followed by extracting the refluxed mixture in a mixture of a polar aprotic organic solvent and an aqueous base, collecting the organic layer, and evaporating the organic solvent to obtain the 1,8-dihaloanthracene.

12. The method of making an antidepressant compound according to claim 10, wherein said step of aminating the respective carbaldehydes comprises mixing the respective carbaldehydes with methylamine in methanol solvent at room temperature in hydrogen atmosphere in the presence of a palladium/charcoal catalyst.

13. The method of making an antidepressant compound according to claim 10, wherein said step of separating the mixture of carbaldehydes by column chromatography comprises eluting the mixture through a silica gel column with a 1:10 ethyl acetate/petroleum ether mobile phase.

14. A compound having the formula:

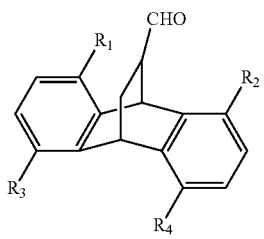

wherein $R_1$ and $R_2$ are either both hydrogen or both halogen, and if $R_1$ and $R_2$ are both hydrogen, $R_3$ and $R_4$ are both halogen and $R_1$ and $R_2$ are both halogen, otherwise both $R_3$ and $R_4$ are hydrogen.

15. The compound according to claim 14, wherein $R_1$ and $R_2$ are both hydrogen and $R_3$ and $R_4$ are both chlorine, the compound having the formula:

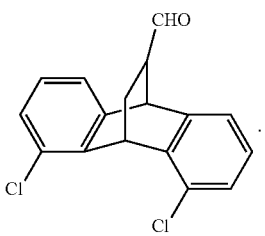 [SMILES: O=CC1CC2c3c(Cl)cccc3C1c1cccc(Cl)c12]

16. The compound according to claim 14, wherein $R_1$ and $R_2$ are both chlorine and $R_3$ and $R_4$ are both hydrogen, the compound having the formula:

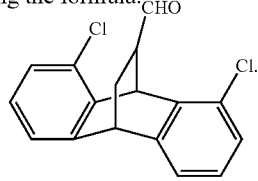

* * * * *